(12) United States Patent
Horst et al.

(10) Patent No.: US 6,841,572 B2
(45) Date of Patent: Jan. 11, 2005

(54) ENVIRONMENTALLY SAFE FUNGICIDE AND BACTERICIDE FORMULATIONS

(75) Inventors: R. Kenneth Horst, Ithaca, NY (US); Leonard R Haupert, Ithaca, NY (US)

(73) Assignee: H&I Agritech, Ithaca, NY (US)

( * ) Notice: Subject to any disclaimer, the term of this patent is extended or adjusted under 35 U.S.C. 154(b) by 0 days.

(21) Appl. No.: 10/369,274

(22) Filed: Feb. 20, 2003

(65) Prior Publication Data

US 2004/0167220 A1 Aug. 26, 2004

(51) Int. Cl.[7] ............................................... A61K 31/19
(52) U.S. Cl. ...................... 514/557; 514/568; 514/574
(58) Field of Search ................................. 514/557, 568, 514/574; 424/405

(56) References Cited

U.S. PATENT DOCUMENTS

| | | | |
|---|---|---|---|
| 3,928,577 A | | 12/1975 | Kochurova et al. |
| 4,851,223 A | | 7/1989 | Sampson |
| 4,915,943 A | * | 4/1990 | Gago et al. ............... 424/93.46 |
| 5,057,326 A | | 10/1991 | Sampson |
| 5,118,444 A | | 6/1992 | Nguyen |
| 5,750,402 A | | 5/1998 | Guri et al. |

FOREIGN PATENT DOCUMENTS

| | | | |
|---|---|---|---|
| DE | 2344887 | * | 3/1975 |
| GB | 2187958 | | 9/1987 |
| JP | 08133914 | * | 5/1996 |
| NZ | 270390 | * | 8/1996 |

OTHER PUBLICATIONS

Zaemey, Magan, and Thompson. "Studies on the effect of fruit–coating polymers and organic acids on growth of *Colletotrichum musae* in vitro and on post–harvest control of anthracnose of bananas." Jun. 1, 1993.

Yaganza, Arul, and Tweddell. "Postharvest application of organic and inorganic salts for the control of potato tuber soft rot." Phytopathology 91:S198. Publication No. P–2001–0039–NEA.

Kitagawa and Kawada. "Effect of Sorbic Acid and Potassium Sorbate on the Control of Sour Rot of Citrus Fruits." Proc. Fla.State Hort. Soc. 97: 133–135.

Hervieux, Yaganza, Arul, and Tweddell, "Effect of Organic and Inorganic Salts on the Development of *Helminthosporium solani*, the Causal Agent of Potato Silver Scurf." Plant Disease/ vol. 86 No. 9, Sep. 2002.

* cited by examiner

*Primary Examiner*—Alton Pryor
(74) *Attorney, Agent, or Firm*—Stuart D. Frenkel

(57) ABSTRACT

Environmentally safe fungicide and bactericide formulations are provided by incorporating one or more preservatives in a mildly acidic aqueous solution. The preservatives include organic acids and the salts and esters thereof but exclude preservatives which can generate sulfur or chlorine-containing compounds.

28 Claims, No Drawings

ENVIRONMENTALLY SAFE FUNGICIDE AND BACTERICIDE FORMULATIONS

FIELD OF THE INVENTION

The invention pertains to environmentally safe fungicide and bactericide formulations and use thereof to control plant pathogens.

BACKGROUND OF THE INVENTION

Fungal and bacterial pathogens can lower yields, reduce quality, negatively affect the aesthetic and economic value and even ultimately destroy plants, crops, pre-harvest fruits, trees, vegetables and grasses.

A broad range of organic molecules have been found to have fungicidal and bactericidal properties and are effectively used for plant disease control. However, many of the currently used pesticides pose a high risk to human health and the environment and are not biodegradable. Since the establishment of the Environmental Protection Act in 1972 there has been an increased concern over the use of toxic chemicals for plant disease control and the dangerous residual potential these toxic products represent. The United States Congress disclosed its concerns with those products with the passage of the Food Quality Protection Act in August, 1996 which requires the U.S. EPA to reassess each existing pesticide by 2006. Because of toxicity concerns, to reduce residues on crops, fruits and vegetables, the application of pesticides shortly before harvest must usually be avoided. Additionally, because of concerns regarding the health of workers, entry into fields or greenhouses shortly after pesticide application is usually prohibited.

Therefore, there is a real need to provide more biocompatible fungicides and bactericides which are, by definition, safe in the environment, non-toxic to humans and animals, and which are rapidly biodegradable.

Because of their safety and efficacy, preservatives have long been used to prevent growth of stray bacteria, fungi and other pathogens in cosmetics, household products, foods and beverages. These materials are thereby effective in preserving products against spoilage by fungal and bacterial contamination and do not present a health or safety hazard when regularly contacted or ingested in minor concentrations. It has been demonstrated that preservatives can prevent storage rot of post-harvest fruits such as bananas, citrus fruit, potatoes and yams caused by fungi and bacteria (Al-Zaemey et al. "Studies on the effect of fruit coating polymers and organic acids on growth of *Colletotrichum musae* in vitro and on postharvest control of anthracnose of bananas". *Mycol. Res* 97: 1463–1468, 1993; Kitagawa, H., Kawada, K. "Effect of sorbic acid and potassium sorbate on the control of sour rot of citrus fruits." *Proc. Ann. Meet. Fla. State Hortic. Soc. s*. Vol 97: 133–135, 1985; Hervieux, V., et al. "Effect of organic and inorganic salts on the development of *Helminthosporium solani*, the causal agent of potato silver scurf." *Plant Dis*. 86: 1014–1018, 2002; Yaganza, E. S. et al. "Postharvest application of organic and inorganic salts for the control of potato tuber soft rot." *Phytopathology* 91: S 198, 2001.)

While it has been suggested that some preservatives may be environmentally safe and effective in controlling plant diseases caused by fungi, the parameters for the usefulness thereof have not been thoroughly explored. U.S. Pat. No. 5,057,326 states that sodium propionate, sodium sorbate and sodium metabisulfite are each known to be fungicidal when used alone at high concentrations. Data are provided which show that, when used alone in fungicide formulations at concentrations of 0.03% to 0.23%, potassium sorbate, sodium propionate or sodium metabisulfite are only marginally effective (25 to 40% reduction) in controlling powdery mildew on spring barley. However, the patent describes the synergistic use of combinations of these water soluble salts to control fungi on growing plants and post-harvest fruits. Thus, data is provided showing that when sodium metabisulfite is mixed with either potassium sorbate or sodium propionate the efficacy is greatly improved (90 to 100% reduction). While sodium metabisulfite is a slightly acidic salt (pH alone between 4.5 and 5.0) combinations with the propionate and sorbate salts would be considerably more basic. The criticality of pH on activity is not suggested. Further, the addition of sodium metabisulfite to a plant fungicide has three potential undesirable side-effects. First, sodium metabisulfite emits sulfur dioxide at acidic pHs creating a potentially toxic atmosphere for humans. Thus it would be undesirable to enter fields or greenhouses immediately after treatment with products containing sodium metabisulfite. Secondly, sulfur dioxide emissions are environmentally undesirable in that they can contribute to acid rain development. Thirdly, residues of sodium sulfite can remain on treated plants. Many people are allergic to sodium sulfite in foods. Therefore, metabisulfite-containing fungicides cannot be applied to fruits and vegetables immediately before harvest.

Similarly, U.S. Pat. No. 4,851,223 discloses the use of preservatives such as sodium metabisulfite, sodium propionate, etc. in a mixture with a coating agent di-1-p-menthene and, optionally, a nonyl phenol ethylene oxide surfactant to control fungi and bacteria on living ornamentals and crop plants. Once again the criticality of pH is not mentioned and the same potential negative safety and environmental effects from metabisulfite exist with this invention as with those of U.S. Pat. No. 5,057,326.

U.S. Pat. No. 5,750,402 discloses the use of potassium sorbate and sodium benzoate as part of a formulation containing the biocide mix of methylchloroisothiazolinone and methylisothiazolinone used to prevent microbial growth in plant tissue culture and plant seed growth media. However, the criticality of pH is not mentioned, indeed both potassium sorbate and sodium benzoate are alkaline salts. As a result, the amounts of potassium sorbate and sodium benzoate needed are high.

When used alone, preservatives would not be expected to be useful in controlling diseases on plants, crops, trees, pre-harvest fruits, flowers, vegetables or grasses. First of all, preservatives are generally growth inhibitory but they are often not very effective in killing fungi or bacteria. Secondly, preservatives are not known to have any plant systemic activity, which is usually associated with effective plant fungicides and bactericides. Thirdly, preservatives do not spread well when applied to plant tissue, leaving large untreated areas where fungi and bacteria can survive. Fourthly, when used in cosmetics, foods and beverages the levels of fungi and bacteria are limited and there is an extended period of time available, sometimes several weeks, for the preservatives to kill the pathogens. In fact when used in preserving cosmetics and foods, it is often not necessary to kill all the bacteria and fungi present. It is often only needed to prevent their further growth and proliferation. On the other hand, in plants there are often high levels of fungi and bacteria that have to be eradicated and the period of time available for activity may be limited due to rain and other prevalent conditions. Optimum conditions for the efficacious use of preservatives on live plants have not been previously reported. Therefore, preservatives are not generally used to provide control of diseases on or in living plants

SUMMARY OF THE INVENTION

The present invention includes products and methods of controlling plant diseases caused by fungal and bacterial pathogens using ingredients commonly used as preservatives in foods, beverages, cosmetics and other products. Preservative compositions of the invention have been found to have exceptional fungicidal and bactericidal activity on many types of fungal and bacterial pathogens commonly found on live plants, crops, trees, pre-harvest fruits, vegetables, grasses, leaves, stems, roots and flowers. The controlled pH formulations have high efficacy at low preservative concentrations. This results in economical products, with minimal likelihood of phytotoxicity to the plant being treated and reduced environmental impact, if any. Thus, products of the invention are environmentally safe and effective in controlling diseases caused by fungi and bacteria and can be used on commercially raised living plants, crops, trees, pre-harvest fruits, vegetables, grasses and ornamentals, as well as on home trees, garden and indoor plants. Because of the proven safety of preservatives and the consequent widespread use thereof in foods and beverages, preservatives used in formulations of the invention can be applied right up to the time of harvest without concern for ill health effects. Also fields and greenhouses treated with these products can immediately be entered without risk to workers.

The invention provides for fungicidally and or bactericidally effective concentrations of one or more preservative compounds in mildly acidic aqueous solutions. The useful preservatives in the form of organic acids, and the salts and esters thereof, are free from salts that can generate potentially toxic sulfur dioxide and/or chlorine-containing gases. Thus, sulfite, thiosulfite, hydrosulfite, metabisulfate, chlorite and other salts that can generate sulfur dioxide or chlorine-containing gases are not among the useful preservations of this invention. Optionally, the preservatives can be used together with one or more surfactants, wetting, sticking and/or spreading agents for treating live plants, crops, trees, pre-harvest fruits, vegetables, leaves, stems, roots and flowers.

A second aspect of the invention is a preservative concentrate formulation, free from sulfite, thiosulfate, hydrosulfite, metabisulfite, chlorite, or other potentially toxic sulfur or chlorine generating salts, which when diluted in water has a pH of between about 2.5 and 6.5, and comprising one or more preservative compounds selected from organic acids, and salts and esters thereof, optionally, together with one or more surfactants, wetting, sticking and/or spreading agents and preferably one or more acidulants.

A third aspect of the invention is a method of treating live plants, crops, trees, pre-harvest fruits, vegetables, grasses, leaves, stems, roots or flowers with mildly acidic aqueous solutions of pH between 2.5 and 6.5, with the preservatives of this invention free from sulfite, thiosulfite, hydrosulfite, metabisulfite, chlorite, or other potentially toxic sulfur- or chlorine-generating salts.

DETAILED DESCRIPTION

The present invention provides for plant, animal, human and environmentally safe fungicide and bactericide treatments for control of plant diseases by the application of solutions of preservative acids or weakly alkaline preservative salts in a buffered acidic aqueous medium. The products are designed to be used while the plants are growing and can be used to control diseases on foliage, stems, flowers and fruits anytime prior to harvest.

More specifically the invention provides for aqueous solutions for treating live plants, crops, trees, pre-harvest fruits, vegetables, leaves, stems, roots and flowers containing fungicidally and/or bactericidally effective concentrations of preservatives dissolved in an acidic aqueous solutions of from pH 2.5 to 6.5, optionally containing a surfactant or other wetting, sticking or spreading agent and being free from sulfite, thiosulfate, hydrosulfite, metabisulfite or other potentially toxic sulfur dioxide-generating salts, as well as free from chlorite or other potentially toxic chlorine-generating salts.

We have found that compounds commonly used as preservatives in cosmetics, household products, foods and beverages are somewhat efficacious in killing pathogens on live plants. However, the quantities of preservative needed are generally quite high. Thus, for example, concentrations of greater than about 2% potassium sorbate are required to kill the plant pathogens *Alternaria solani, Botrytis cinerea, Fusarium nygamai*. This makes the use of such compounds economically unfeasible for this use. Also high concentrations of these compounds going into the environment increases the potential environmental impact and increases the loading of organic materials needing biodegradation in lakes and streams.

Secondly, when sprayed on plants, solutions of preservatives tend to bead up and do not spread or stick on the foliage or flowers being treated. In the absence of spreading and adhesion the preservatives may not make sufficient contact to control plant pathogens. This factor is less critical with conventional systemic pesticides which are absorbed into the plant and spread through the circulatory system. Therefore one novel aspect of this invention is the effective use of a surfactant spreader, wetter or sticker system.

We have found that the compounds commonly used as preservatives in cosmetics, household products, foods and beverages can be made to be much more highly efficacious in controlling pathogens on live plants if they are used in the mildly acidic pH range of between 2.5 and 6.5, preferably from 3.0 to 5.5, more preferably from 3.5 to 5.0, most preferably from 4.0 to 4.6. Effectiveness is enhanced if the preservatives are also combined with at least 0.001% surfactant, wetting, spreading and/or sticking agent.

Preservatives useful in this invention are selected from one or more organic acids, and the salts and esters thereof. Non-limiting examples include (a) sorbic, benzoic and lactic acids (b) the sodium, potassium, calcium and ammonium salts of benzoic acid, sorbic acid, hydroxymethyl glycinic acid, lactic acid and propionic acid and (c) methyl, ethyl, propyl and butyl paraben.

The concentration of preservative to be used is an amount sufficient to control the fungal or bacterial species targeted. Generally the concentration needed is between from about 0.1 mM to about 10 mM of preservative or from approximately 0.001% to about 0.2% W/V of the aqueous treatment solution. Preferably the concentration of preservative used is between about 0.005% to about 0.1% W/V.

An important aspect of the invention is the pH of the treatment solution. The pH of the treatment solution should be between about 2.5 and 6.5, preferably from 3.0 to 5.5, more preferably from 3.5 to 5.0, most preferably from 4.0 to 4.6. At a pH below the desired range, the treatment solutions become irritating to the skin and eyes, more phytotoxic to the plants being treated and corrosive to equipment. At pHs above the desired range, the efficacy drops off and much higher concentrations of preservatives are needed to eradicate or prevent disease.

While not always essential when using higher concentrations of sorbic, benzoic or lactic acids, the addition of other acidic ingredients is preferable to ensure that the aqueous treatment solution is within the desirable pH range. Acidulants are virtually always needed when utilizing salts of the acidic preservatives and any of the parabens. Examples of suitable acidulants are citric acid, tartaric acid, malic acid, adipic acid, fumaric acid, succinic acid, sodium bisulfate, potassium bisulfate, ammonium bisulfate, boric acid, phosphoric acid. The mildly acidic mono alkali metal and ammonium salts of citric acid, tartaric acid, malic acid, adipic acid, fumaric acid, succinic and phosphoric acids can also be used. Preferable concentrations of acidulant are from about 0.001% to about 0.2%, more preferably from 0.01% to about 0.1%.

An effective adjuvant to the preservative compositions of the invention is the use of surfactants, wetting, spreading and/or sticking agents. These materials ensure that the applied preservatives spread and adhere to the foliage, flowers and other parts of the plants being treated. In the absence of such materials the treatment solution may bead up, resulting in insufficient contact made between the preservative and pathogen. We have also found, surprisingly that the anti-microbial activity of the preservative system is enhanced in the presence of surfactants and lower concentrations of preservatives can often be effectively used.

Any surfactant can be used. However, preferred surfactants are those that are anionic which tend to be relatively non-toxic and non-irritating to humans and have low phytotoxicity to treated plants. Most preferred are the alkali metal and ammonium alkyl sulfates, dialkyl sulfosuccinates, alkylaryl sulfonates, alkyl sulfonates, alkyl ether sulfates and alkyl phosphate esters with alkyl chain lengths from about 8 to about 18. Alkali metal and ammonium alkyl carboxylate salts can also be used. However, the carboxylate salts are more prone to react with hard water ions. Additionally, amphoteric salts could also be used but these salts tend to be more expensive. While less desirable, nonionic surfactants such as the ethoxylated alcohols and phenols can also be used. However, the concentration employed must be limited to avoid phytotoxicity. For environmental reasons it is desirable to select biodegradable surfactants which rapidly leave the environment.

Preferred surfactants are the alkali metal and ammonium alkyl sulfates and alkali metal and ammonium dialkyl sulfosuccinates. Particularly preferred are combinations of the two, for example sodium lauryl sulfate or sodium myristyl sulfate mixed with sodium dioctyl sulfosuccinate or sodium didecyl sulfosuccinate.

When used, the total amount of surfactant provided in the treatment solution is between about 0.001% to about 0.2%, preferably 0.01% to about 0.1% W/V.

Another feature of the invention is that formulations and methods of the invention do not utilize sulfites or other sulfur dioxide generated salts. Sodium metabisulfite, for example, has known mild anti-fungal properties. However, particularly in acidic solutions of the invention metabisulfite and other sulfites can generate sulfur dioxide gas with greater amounts of the gas being generated as the pH is lowered. Sulfur dioxide is irritating to the skin, eyes and respiratory tract and has a threshold limit value (TLV) as low as 2 ppm. Furthermore, the generation of sulfur dioxide from acidic sulfite solutions could negatively impact the environment by contributing to acid rain. Additionally, sulfites themselves are known to cause allergic reactions in some individuals. Foods containing sulfites require warning labels. In addition high levels of sulfites in foods and beverages can create off flavors. Therefore, sulfite residues on fruits and vegetables should be avoided. Likewise, the formulations of this invention do not utilize chlorine gas-generating salts such as calcium hypochlorite and like chlorine-containing salts.

Another aspect of the invention is the provision of concentrate formulations which can be diluted in water for use in the treatments of plants, crops, pre-harvest fruits and flowers. The concentrate formulations consist of from about 0.5 to about 99%, preferably 10% to 90% of one or more preservative compounds of this invention and preferably from about 0.25% to about 90%, more preferably from 5% to 80% of one or more surfactants, wetting, sticking and/or spreading agents and from about 0% to about 90%, preferably from 5 to 80% of one or more acidulants. It is important that the concentrate formulations of the invention have a pH of from about 2.5 to 6.5, preferably from 3.0 to 5.5, more preferably from 3.5 to 5.0, most preferably from 4.0 to 4.6 when diluted to usage concentration in water.

Optionally the concentrate can also contain diluants, flow aids, anti-caking agents, solubilizing agents, dispersants, colorants, fragrances and other adjuvants. The concentrate can be in any form including a powder, a tablet or a liquid.

Prior to use, the concentrate formulation is diluted in water to provide a concentration of from about 0.002% to about 0.2%, preferably from about 0.01% to about 0.1%, of the preservative material.

Another aspect of the invention is the method of using the inventive formulations on live plants, crops, pre-harvest fruits or flowers. It is anticipated that the products of this invention would be applied in the form of a spray using various types of application equipment. Land based application equipment could include hand or backpack sprayers, truck or tractor mounted sprayers and those towed behind such equipment, and by the addition of concentrated product to irrigation and watering systems. These systems utilize from 20 to 200 gallons of solution per acre. Airborne sprayers mounted on airplanes and helicopters utilize from 5 to 20 gallons of solution per acre.

The formulations and methods of the invention can be used to prevent or eradicate a broad range of fungal infections including powdery mildews such as *Erysiphe sp.* and *Sphaerotheca sp.*, downy mildews such as *Bremia sp.*, and *Peronospora sp.*, black spot including *Diplocarpon sp.*, blights such as *Alternaria sp.* and *Diplodia sp.*, cankers such as *Penicillium sp.* and *Coniothyrium sp.*, leaf curl such as *Taphrina sp.*, leaf spot such as *Botrytis sp.* and *Rhytisma sp.*, rots such as *Aspergillus sp., Fusarium sp., Rhizoctonia sp., Pythium sp., Phytophthora sp. Sclerotinia sp.*, rusts such as *Puccinia sp., Cronartium sp.*, scabs such as *Venturia sp.* and smuts such as *Urocystis sp*. Formulations and methods of the invention are also effective against various bacterial infections including the *Erwinia sp., Pseudomonas sp. and Xanthomonas sp.* types. Specific non-limiting examples of pathogens are *Alternaria solani, Botrytis cinerea, Cercospora zeae-maydis, Colletotrichum graminicola, Fusarium moniliforme, Fusarium nygamai, Fusarium proliferatum, Phytophthora infestans, Pythium ultimum, Rhizoctonia solani, Rhytisma acerinum, Sclerotinia sclerotiorum, Sclerotinia homeocarpa, Erwinia carotovora* subsp. *carotovora* and *Xanthomonas campestris* subsp. *phaseoli* etc.

Methods of use and products of the invention are suitable for treating all types of plants, crops, trees, pre-harvest fruits, vegetables, grasses, leaves, stems, roots and flowers. For example products of the invention can be used to prevent or eradicate fungal and bacterial growth on vegetables such as lettuces, cabbage, spinach, cauliflower, cucurbits, tomatoes, beans and peas; trees and their pre-harvest fruit such as apples, pears, bananas, almond, olive, citrus, date, fig, plum, oak, ash, maple, elm, birch and sycamore; vines such as grape; bushes such as gooseberry, mulberry, blackcurrant and blueberry; other pre-harvest fruits such as strawberries and melons; flowering and non-flowering ornamentals such as roses, poinsettias, tulips, irises, crocuses, daffodils, ivies and chrysanthemums; root vegetables such as carrots, tubers, parsnips, turnips and beats; crops such as various grains, corn, wheat, rye, oats, sesame seed, spelt and sunflowers; legumes such as beans and peanuts as well as grasses, sugar cane, cotton, rice etc.

Significant advantages of methods and formulations of the invention include good efficacy in preventing and eradicating a broad range of plant pathogens. The ingredients used also have excellent safety profiles with long histories of use. Since the ingredients are widely used, foods, fruits and vegetables can be treated with the formulations right up to harvest without the potential to leave unhealthy residues. Fields and greenhouses can be treated without limiting the entry of workers immediately after application. The amounts of materials used are very small and they are biodegradable and therefore are rapidly eliminated from the environment.

The following demonstrates various aspects of the invention.

EXAMPLES 1–3

In vitro studies were performed to determine the effect of pH on the cidal activity of potassium sorbate against various plant pathogens. The ingredients to be tested were mixed into melted sterilized PDA (potato dextrose agar), cooled to about 55° C., plated onto petri dishes and allowed to solidify. The plates were seeded with plugs of inoculum fungi. The plates were then examined after 2, 4 and 6 days. After one week, plugs showing no growth were removed and placed into untreated solidified PDA to determine viability of the fungi. Viability was determined after 2 and 4 days.

Results of in vitro tests using potassium sorbate and citric acid to control fungal plant pathogens

| Pathogen | Control A | Example 1 | Example 2 | Example 3 |
|---|---|---|---|---|
| | Concentration of potassium sorbate and citric acid in mM with solution pH. | | | |
| | Pot. Sorbate 10.0 mM No pH adjust.; pH 7.8 | Pot. Sorbate 5.0 mM; citric acid 3.6 mM; pH 4.1 | Pot. sorbate 1.4 mM; citric acid 2.6 mM; pH 4.1 | Pot. Sorbate 1.0 mM; citric acid 2.4 mM; pH 4.1 |
| Alternaria solani | 0 | Fd | Fs | 0 |
| Botrytis cinerea | 0 | Fd | Fs | Fs |
| Cercospora zeaemay. | — | Fd | Fd | Fd |
| Colletotrichum gram. | 0 | Fd | Fd | Fd |
| Fusarium moniliforme | Fs | Fd | Fs | Fs |
| Fusarium nygamai | Fs | Fd | Fs | Fs |
| Fusarium proliferatum | 0 | Fd | Fs | Fs |
| Rhytisma acerinum | 0 | Fd | Fs | Fs |

— Not Tested
0 - no activity, mycelial growth occurred
Fs - Fungistatic activity
Fd - Fungicidal effect - mycelial growth was completely inhibited The results show that potassium sorbate at a concentration of 10 mM (0.15% solution) is inactive or at best exhibits only static activity against plant pathogens at a pH above 7.0. However, when the pH is lowered to 4.1 cidal activity is noted against the broad range of plant pathogens tested when the preservative is used at only 5 mM (0.075% solution). Cidal activity against two pathogens is maintained down to 1 mM sorbate or lower concentrations at this pH.

EXAMPLES 4–6

Additional in vitro studies demonstrate the unexpected cidal boosting effect of surfactants (SDSS=sodium dioctyl sulfosuccinate, SLS=sodium lauryl sulfate) against various plant pathogens when potassium sorbate is used. The ingredients to be tested were mixed into melted sterilized PDA, cooled to about 55° C., plated onto petri dishes and allowed to solidify. The plates were seeded with plugs of inoculum fungi. The plates were then examined after 2, 4 and 6 days. After one week, plugs showing no growth were removed and placed into untreated solidified PDA to determine viability of the fungi. Viability was determined after 2 and 4 days.

Results of in vitro tests using potassium sorbate/citric acid formulations to control fungal plant pathogens.

| Pathogen | Control B | Example 4 | Example 5 | Example 6 |
|---|---|---|---|---|
| | Potassium Sorbate Concentration with Solution pH. | | | |
| | Pot. Sorbate 10.0 mM, no pH adjustment; pH 7.8 | Pot. Sorbate 5.0 mM; pH adjusted to pH 4.1; see 1 below | Pot. Sorbate 1.4 mM; pH adjusted & surfactants added; pH 4.3; see 2 below | Pot. Sorbate 1.0 mM; pH adjusted & surfactants added; pH 4.3; see 3 below |
| Alternaria solani | 0 | Fd | 80% growth reduct. | 80% growth reduct. |
| Botrytis cinerea | 0 | Fd | Fd | Fd |
| Cercospora zeaemay. | — | Fd | Fd | Fd |
| Colletotrichum gram. | 0 | Fd | Fd | Fd |

-continued

Results of in vitro tests using potassium sorbate/citric acid formulations to control fungal plant pathogens.

| | Control B | Example 4 | Example 5 | Example 6 |
|---|---|---|---|---|
| | Potassium Sorbate Concentration with Solution pH. | | | |
| Pathogen | Pot. Sorbate 10.0 mM, no pH adjustment; pH 7.8 | Pot. Sorbate 5.0 mM; pH adjusted to pH 4.1; see 1 below | Pot. Sorbate 1.4 mM; pH adjusted & surfactants added; pH 4.3; see 2 below | Pot. Sorbate 1.0 mM; pH adjusted & surfactants added; pH 4.3; see 3 below |
| Fusarium moniliforme | Fs | Fd | Fd | Fd |
| Fusarium nygamai | Fs | Fd | Fd | Fd |
| Fusarium proliferatum | 0 | Fd | Fd | Fd |
| Rhytisma acerinum | 0 | Fd | Fd | Fd |

— Fungus not tested
0 - no activity, mycelial growth occurred
Fs - Fungistatic activity
Fd - Fungicidal effect - mycelial growth was completely inhibited
1 - Formulation consists of 5.0 mM pot. Sorbate and 3.0 mM citric acid,
2 - Formulation consists of 1.4 mM pot. Sorbate, 2.6 mM citric acid, SLS 0.0295% + SDSS 0.0587%
3 - Formulation consists of 1.0 mM pot. Sorbate, 2.4 mM citric acid, SLS 0.0295% + SDSS 0.0587%

A comparison of Examples 5 and 6 (surfactants added) with Examples 2 and 3 (no surfactants) show that in the pH range of the invention the cidal activity of potassium sorbate is enhanced in presence of surfactants. Thus 7 out of 8 pathogens are killed at pH 4.1, using potassium sorbate at the reduced concentration of 1 mM (0.015%).

EXAMPLES 7 AND 8

The following shows the effect of reducing the pH on the cidal activity of sodium benzoate. The ingredients to be tested were mixed into melted sterilized PDA, cooled to about 55° C., plated onto petri dishes and allowed to solidify. The plates were seeded with plugs of inoculum fungi. The plates were then examined after 2, 4 and 6 days. After one week, plugs showing no growth were removed and placed into untreated solidified PDA to determine viability of the fungi. Viability was determined after 2 and 4 days.

Results of in vitro tests using sodium benzoate pH adjusted with citric acid to control fungal plant pathogens.

| | Control C | Example 7 | Example 8 |
|---|---|---|---|
| | Concentration of sodium benzoate in mM. | | |
| Pathogen | 5.0 mM no pH adjustment; pH 7.8 | 5.0 mM + 2.1 mM citric acid; pH 4.6 | 5.0 mM + 3.3 mM citric acid; pH 4.2 |
| Alternaria solani | 0 | 0 | Fd |
| Botrytis cinerea | 0 | 0 | Fd |
| Cercospora zeaemaydis | — | Fd | Fd |
| Colletotrichum graminicola | 0 | Fd | Fd |

-continued

Results of in vitro tests using sodium benzoate pH adjusted with citric acid to control fungal plant pathogens.

| | Control C | Example 7 | Example 8 |
|---|---|---|---|
| | Concentration of sodium benzoate in mM. | | |
| Pathogen | 5.0 mM no pH adjustment; pH 7.8 | 5.0 mM + 2.1 mM citric acid; pH 4.6 | 5.0 mM + 3.3 mM citric acid; pH 4.2 |
| Fusarium moniliforme | 0 | Fs | Fd |
| Fusarium nygamai | 0 | Fd | Fd |
| Fusarium proliferatum | 0 | Fd | Fd |
| Rhytisma acerinum | 0 | Fd | Fd |
| Sclerotinia homoeocarpa | 0 | 0 | Fd |
| Sclerotinia sclerotiorum | 0 | Fd | Fd |

— not tested
0 - no activity, mycelial growth occurred
Fs - Fungistatic activity
Fd - Fungicidal effect - mycelial growth was completely inhibited In these examples sodium benzoate at 5 mM (0.072% solution) was ineffective in controlling the plant pathogens when used at a pH above 7.0. However, when the pH was reduced to 4.6 cidal activity was found in 6 out of 10 species. Cidal activity increased at pH 4.1 with 10 out of 10 species tested being killed at this pH.

EXAMPLES 9 AND 10

The following examples illustrate the effectiveness of the treatment solutions of the invention in vivo. Bentgrass was seeded in a peat-like mix and covered with a plastic lid. Germinated seedlings were inoculated with 1 rye grain infected with *S. homeocarpa*. Treatments were made 48 hours after inoculation using a fine mist. Examinations were made after 10 days.

Results of in vivo tests using potassium sorbate/sodium benzoate formulations to control dollar spot (*Sclerotinia homeocarpa*) on bentgrass turf.

| | Disease Rating | |
|---|---|---|
| Treatment Formulation | Replicate 1 | Replicate 2 |
| Pot. Sorbate-1.0 mM; Citric acid-2.4 mM; SLS 0.0295% + SDSS 0.0587%; pH 4.3 Example 9 | 0 | 1 |
| Sod. Benzoate 5.0 mM; Citric acid 3.6 mM; SLS 0.0295% + SDSS 0.0587%; pH 4.3 Example 10 | 0 | 1 |
| Control - Water Treatment Control D | 5 | 5 |

Disease Rating Scale
0 - No infection
1 - !0% or less infection infection
2 - 33% or less infection
3 - 50% or less infection
4 - 75% or less
5 - 90% or more infection The results show the efficacy of the formulations of the invention against dollar spot on live bentgrass turf.

EXAMPLES 11, 12 AND 13

The following show effect of treatment solutions of the invention against plant bacteria. Bacteria from bacteria isolate were dispersed in water. Serial dilutions were then made. One ml of dispersion was added to 10 ml melted nutrient agar to which had been added the treatment. Bacterial counts were made after 7 days.

Results of in vitro tests using potassium sorbate/sodium benzoate formulations to control plant bacterial pathogens.

| | Bacterial Colonies | | | | | |
|---|---|---|---|---|---|---|
| | *Erwinia carotovora* subsp. *carotovora* | | | *Xanthomonas campestris* subsp. *phaseoli* | | |
| Treatment Formulation | 1:1000 Dilution | 1:10,000 Dilution | 1:50,000 Dilution | 1:1000 Dilution | 1:10,000 Dilution | 1:50,000 Dilution |
| Pot. Sorbate-1.0 mM; Citric acid-2.4 mM; SLS 0.0295% + SDSS 0.0587%; pH 4.3 Example 11 | 0 | 0 | 0 | 0 | 0 | 0 |
| Pot. Sorbate-1.4 mM; Citric acid-2.6 mM; SLS 0.0295% + SDSS 0.0587%; pH 4.3 Example 12 | 0 | 0 | 0 | 0 | 0 | 0 |
| Sod. Benzoate 5.0 mM; Citric acid 3.6 mM; SLS 0.0295% + SDSS 0.0587%; pH 4.3 Example 13 | 0 | 0 | 0 | 0 | 0 | 0 |
| Control - Nutrient agar only Control E | Complete Coloniz. | Complete Coloniz. | 77 | Complete Coloniz. | 11 | 13 |

EXAMPLES 14–17

The following table shows examples of treatment solutions for applying to live plants, crops, pre-harvest fruit and flowers.

| | Ex-14 % | Ex-15 % | Ex-16 % | Ex-17 % |
|---|---|---|---|---|
| Citric acid | 0.070 | | | 0.100 |
| Sodium benzoate | 0.070 | | | |
| Sodium lauryl sulfate | 0.020 | 0.030 | 0.040 | |
| Sodium didecylsulfosuccinate | 0.040 | 0.030 | | 0.050 |
| Tartaric acid | | 0.004 | 0.002 | |
| Potassium sorbate | | 0.002 | | |
| Methyl paraben | | | 0.002 | |
| Propyl paraben | | | 0.001 | |
| Calcium propionate | | | | 0.100 |
| Water | 99.800 | 99.934 | 99.955 | 99.750 |

EXAMPLES 18–21

The following provides examples of concentrate treatments for dilution prior to application to live plants, crops, pre-harvest fruits and flowers.

| | Ex-18 % | Ex-19 % | Ex-20 % | Ex-21 % |
|---|---|---|---|---|
| Citric acid | 7.000 | | | 40.000 |
| Sodium benzoate | 7.000 | | | |
| Sodium lauryl sulfate | 2.000 | 45.000 | 80.000 | |
| Sodium didecylsulfosuccinate | 2.000 | 45.000 | | 20.000 |
| Tartaric acid | | | 8.000 | |
| Sorbic acid | | 10.000 | | |
| Ethyl paraben | | | 8.000 | |
| Propyl paraben | | | 4.000 | |
| Calcium lactate | | | | 40.000 |
| Water | 82.000 | | | |

Example 18 is a liquid concentrate which is diluted in water to a concentration of from 0.5 to 2% prior to use. Examples Ex-19, Ex-20 and Ex-21 are concentrate powders which are diluted to a concentration of 0.05 to 0.2% prior to use. Example E-20 is diluted to 0.03 to 0.15% prior to use. Example E-21 is diluted to a concentration of 0.002 to 0.01% prior to use.

What is claimed is:

1. Aqueous solution for treating live plants, crops, trees, pre-harvest fruits, vegetables, leaves, stems, roots and flowers having a pH of between 4.0 and 6.5 and consisting essentially of fungicidally and/or bactericidally effective concentrations of one or more preservative compounds selected from the group consisting of sorbic, benzoic and lactic acid; the sodium, potassium, calcium and ammonium salts of benzoic, sorbic, hydroxymethyl glycinic, lactic and propionic acid; and methyl, ethyl, propyl and buryl paraben, at least one anionic surfactant, and optionally an acidulant.

2. The solution of claim 1 having a pH between 4.0 and 4.6.

3. The solution of claim 1 where the concentration of preservative is from 0.001 to 0.2% by weight.

4. The solution of claim 1 where the concentration of preservative is from 0.005 to 0.1% by weight.

5. The solution of claim 1 also containing an acidulant.

6. The solution of claim 5 in which the acidulant is one or more of citric acid, malic acid, tartaric acid, adipic acid, succinic acid or fumaric acid, or the monosodium, monopotassium or monoammonium salts thereof.

7. The solution of claim 5 in which the acidulant is either phosphoric acid or the mono-sodium ammonium or potassium salt thereof.

8. The solution of claim 5 in which the acidulant is either sodium, potassium or ammonium bisulfate.

9. The solution of claim 1 containing 0.001% and 0.2% by weight of one or more of said anionic surfactants.

10. The solution of claim 1 wherein said at least one anionic surfactant is one or more alkali metal and ammonium alkyl sulfates, dialkyl sulfosuccinates, alkylaryl sulfonates, alkyl sulfonates, alkyl ether sulfates and alkyl phosphate esters with alkyl chain lengths from 8 to 18.

11. The solutions of claim 9 in which the concentration of said at least one anionic surfactant is from 0.01% to 0.1% by weight.

12. The solution of claim 10 wherein said at least one anionic surfactant is either sodium lauryl sulfate, sodium myristyl sulfate, sodium dioctyl sulfosuccinate, sodium didecyl sulfosuccinate or mixtures thereof.

13. The solution of claim 5 containing 0.001% and 0.2% by weight of one or more said anionic surfactants.

14. A method of treating live plant life comprising plants, crops, trees, pre-harvest fruits, vegetables, leaves, stems, roots and flowers to kill fungal or bacterial pathogens by contacting said plant life with a mildly acidic aqueous solution of pH between 4.0 and 6.5, and consisting essentially of one or more fungicidally and or bactericidally effective concentrations of one or more preservative compounds selected from the group consisting of sorbic, benzoic and lactic acid; the sodium, potassium, calcium and anlinonium salts of benzoic, sorbic, hydroxymethyl glycinic, lactic and propionic acid; and methyl, ethyl, propyl and butyl paraben, at least one anionic surfactant, and optionally an acidulant.

15. The method of claim 14 in which the solution has a pH between 4.0 and 4.6.

16. The method of claim 14 wherein the concentration of preservative is from 0.001 to 0.2% by weight.

17. The method of claim 14 wherein the concentration of preservative is from 0.005 to 0.1% by weight.

18. The method of claim 14 in which the solution also contains an acidulant.

19. The method of claim 18 in which the acidulant is citric acid, malic acid, tartaric acid, adipic acid, succinic acid or fumaric acid, or the monosodium, monopotassium or monoammonium salts thereof.

20. The method of claim 18 in which the acidulant is either phosphoric acid or the mono-sodium ammonium or potassium salt thereof.

21. The method of claim 18 in which the acidulant is sodium, potassium or ammonium bisulfate.

22. The method of claim 14 wherein said anionic surfactant is one or more alkali metal and ammonium alkyl sulfates, dialkyl sulfosuccinates, alkylaryl sulfonates, alkyl sulfonates, alkyl ether sulfates and alkyl phosphate esters with alkyl chain lengths from 8 to 18.

23. The method of claim 14 in which the concentration of said anionic surfactant is from 0.001% to 0.2% by weight.

24. The method of claim 22 in which the anionic surfactant is sodium lauryl sulfate, sodium myristyl, sodium dioctyl sulfosuccinate, sodium didecyl sulfosuccinate or mixtures thereof.

25. The method of claim 14 wherein said fungal or bacterial pathogens cause plant disease in the form of powdery mildew, downy mildew, black spot, blight, canker, leaf curl, leaf spot, rot, rust, scab, smut and bacteria on living plants.

26. The method of claim 14 wherein said solution is applied as a spray.

27. The method of claim 14 wherein said plant life is treated with said aqueous solution after said plant life is contacted with said fungal or bacterial pathogens.

28. The method of claim 14 wherein said plant life is treated with said aqueous solution prior to when said plant life is contacted with said fungal or bacterial pathogens.

* * * * *